(12) United States Patent
Salowitz et al.

(10) Patent No.: US 10,610,611 B2
(45) Date of Patent: Apr. 7, 2020

(54) WATER-BASED FRAGRANCE COMPOSITION, FRAGRANCE DELIVERY DEVICE, AND METHOD OF PROVIDING A LONG-LASTING SCENT

(71) Applicant: S. C. JOHNSON & SON, INC., Racine, WI (US)

(72) Inventors: Rachel E. Salowitz, Whitefish Bay, WI (US); Paul A. Clark, Racine, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 15/745,952

(22) PCT Filed: Jul. 19, 2016

(86) PCT No.: PCT/US2016/042935
§ 371 (c)(1),
(2) Date: Jan. 18, 2018

(87) PCT Pub. No.: WO2017/015273
PCT Pub. Date: Jan. 26, 2017

(65) Prior Publication Data
US 2018/0207309 A1    Jul. 26, 2018

Related U.S. Application Data

(60) Provisional application No. 62/194,653, filed on Jul. 20, 2015.

(51) Int. Cl.
*A61L 9/01*    (2006.01)
*A61L 9/12*    (2006.01)
(Continued)

(52) U.S. Cl.
CPC .............. *A61L 9/01* (2013.01); *A61L 9/127* (2013.01); *A61L 9/14* (2013.01); *A61L 9/032* (2013.01);
(Continued)

(58) Field of Classification Search
CPC ... A61L 9/01; A61L 9/127; A61L 9/14; A61L 2209/21; A61L 9/037; A61L 9/032; A61L 9/122; A61L 2209/134
See application file for complete search history.

(56) References Cited

U.S. PATENT DOCUMENTS 6,013,248 A * 1/2000 Luebbe ................. A61K 8/042
424/400
6,454,876 B1    9/2002 Ochomogo et al.
(Continued)

FOREIGN PATENT DOCUMENTS

DE    19728670 A1    1/1998
EP    2832453 A1    2/2015
(Continued)

OTHER PUBLICATIONS

International Search Report and Written Opinion, International Application No. PCT/US2016/042935, dated Oct. 24, 2016, 16 pages.
(Continued)

*Primary Examiner* — Pamela H Weiss
(74) *Attorney, Agent, or Firm* — Quarles & Brady LLP

(57) ABSTRACT

A water-based fragrance composition comprises at least about 67 wt % water and between about 5 and about 17 wt % of a first organic solvent, wherein the first organic solvent comprises one or more relatively volatile, water soluble, low molecular weight organic compound(s) having a boiling point less than about 100° C. The water-based fragrance composition further comprises about 5 wt % or less of at
(Continued)

Figure 1:
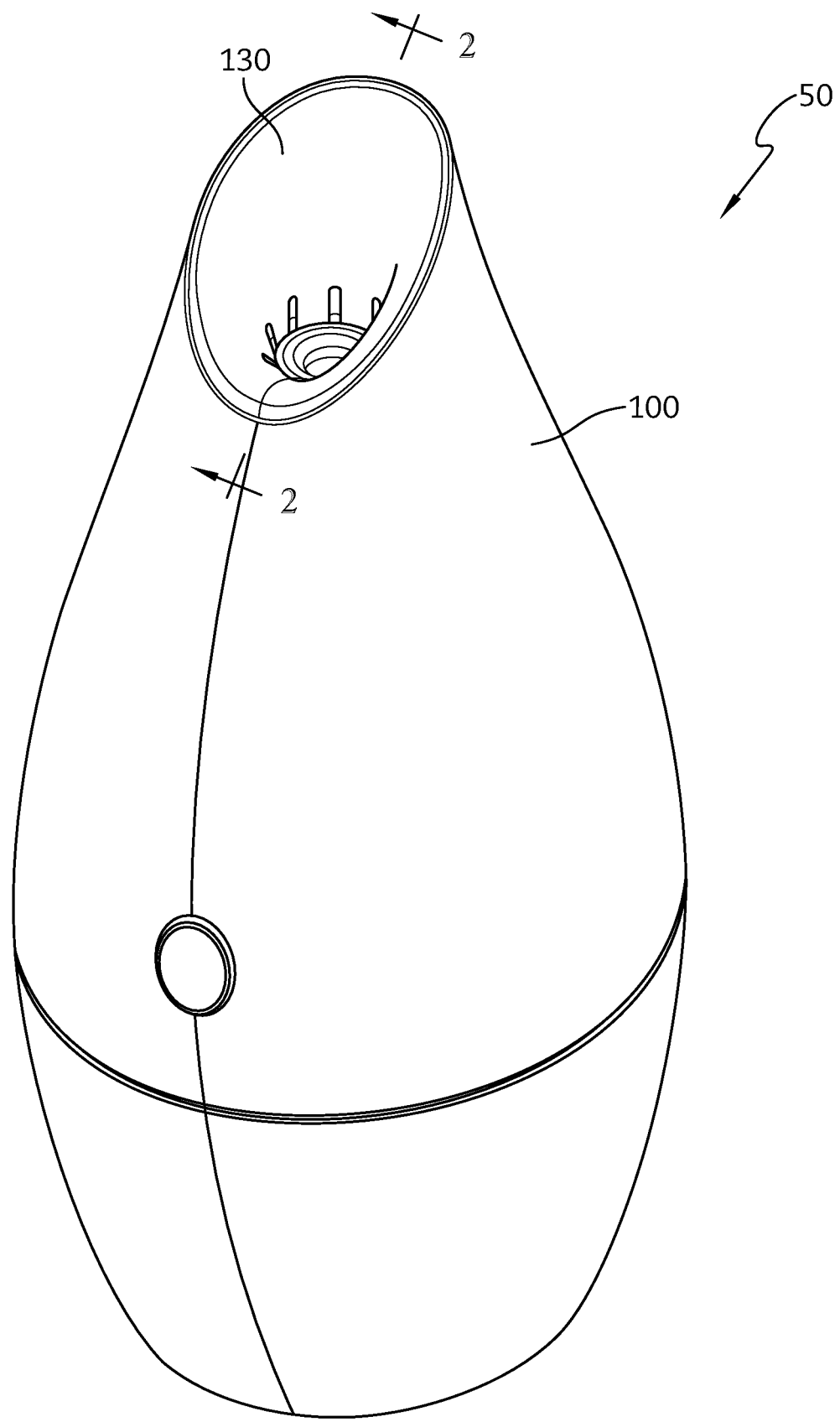
Figure 2:
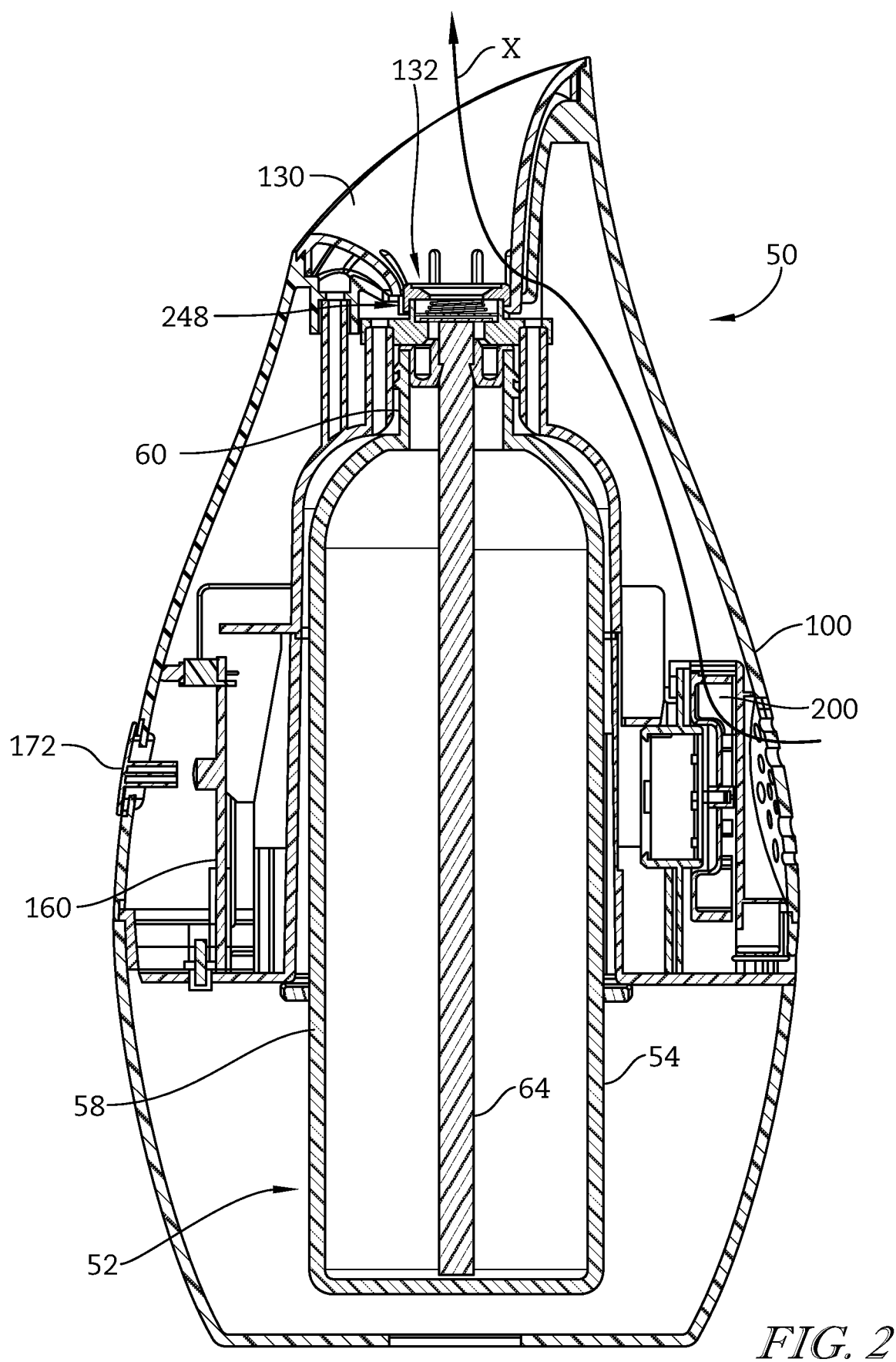

least one fragrance formulation and between about 0 and about 22 wt % of a second organic solvent, wherein the second organic solvent comprises one or more moderately volatile, water soluble organic compound(s) having a boiling point greater than or equal to about 100° C. and less than or equal to about 300° C.

10 Claims, 2 Drawing Sheets

(51) Int. Cl.
    *A61L 9/14*     (2006.01)
    *A61L 9/03*     (2006.01)

(52) U.S. Cl.
    CPC ............... *A61L 9/037* (2013.01); *A61L 9/122* (2013.01); *A61L 2209/21* (2013.01)

(56) References Cited

U.S. PATENT DOCUMENTS

| | | | | |
|---|---|---|---|---|
| 6,503,413 B2* | 1/2003 | Uchiyama | ............... | C11D 1/62 252/8.61 |
| 6,613,244 B2* | 9/2003 | Fry | ..................... | D06M 13/005 252/8.61 |
| 6,780,403 B1 | 8/2004 | Yamashita et al. | | |
| 6,833,342 B2 | 12/2004 | Woo et al. | | |
| 7,550,416 B2* | 6/2009 | Woo | .......................... | A61L 9/01 510/102 |
| 2008/0003193 A1 | 1/2008 | Rebrovic | | |
| 2008/0023569 A1 | 1/2008 | O'Leary et al. | | |
| 2011/0051983 A1 | 3/2011 | Jörgensen | | |
| 2011/0150817 A1* | 6/2011 | Woo | .......................... | A61L 9/01 424/76.21 |
| 2012/0027713 A1* | 2/2012 | Nguyen | ..................... | A61L 2/18 424/76.8 |
| 2012/0046167 A1* | 2/2012 | Sowa | ..................... | A01N 31/02 504/100 |
| 2012/0097754 A1 | 4/2012 | Vlad et al. | | |
| 2012/0301421 A1* | 11/2012 | Hecking | ................... | A61L 9/14 424/76.8 |
| 2014/0148339 A1* | 5/2014 | Smejkal | .............. | C07D 255/02 504/103 |
| 2015/0104348 A1 | 4/2015 | Nichols et al. | | |

FOREIGN PATENT DOCUMENTS

| | | | | | |
|---|---|---|---|---|---|
| EP | 3023090 | A1 | 5/2016 | | |
| JP | 2001095907 | A | 4/2001 | | |
| JP | 2003508582 | A | 3/2003 | | |
| JP | 2006513815 | A | 4/2006 | | |
| JP | 2008534043 | A | 8/2008 | | |
| JP | 2009520873 | A | 5/2009 | | |
| JP | 2013208581 | A | 10/2013 | | |
| KR | 10-2001-0043228 | A | 5/2001 | | |
| WO | WO-02099179 | A2 * | 12/2002 | ............... | A61L 9/01 |
| WO | 2004098662 | A1 | 11/2004 | | |
| WO | WO2004098662 | A1 | 11/2004 | | |
| WO | WO-2006131689 | A1 * | 12/2006 | ............... | C11D 1/02 |
| WO | 2009058305 | A1 | 5/2009 | | |
| WO | WO2009058305 | A1 | 5/2009 | | |
| WO | WO-2009074114 | A1 * | 6/2009 | ............. | A01N 25/04 |
| WO | 2011138620 | A1 | 11/2011 | | |
| WO | WO2011138620 | A1 | 11/2011 | | |

OTHER PUBLICATIONS

Examination Report No. 3, Australian Government, dated May 8, 2018.
First Office Action issued in Japanese Application No. 2018-502724, dated May 28, 2019, 9 pages.
Grounds for Rejection issued in Korean Application No. 10-2018-7004238, dated Sep. 1 2019, 32 pages.

* cited by examiner

WATER-BASED FRAGRANCE COMPOSITION, FRAGRANCE DELIVERY DEVICE, AND METHOD OF PROVIDING A LONG-LASTING SCENT

CROSS REFERENCE TO RELATED APPLICATIONS

This application is a national stage entry of International Application No. PCT/US2016/042935, filed on 19 Jul. 2016, which claims the benefit of U.S. Provisional Patent Application No. 62/194,653, filed on 20 Jul. 2015, the disclosures of which are hereby incorporated by reference in their entirety.

BACKGROUND

1. Field of the Disclosure

The present disclosure relates generally to volatile material dispensers and, more particularly, to water-based fragrance compositions, volatile material dispensers for emission of water-based fragrance compositions, and methods for emitting long-lasting scent.

2. Description of the Background

Various volatile material dispensers are known in the prior art, most of which deliver fragrance to the air by a number of different mechanisms, including, for example: (1) the fragrance is sprayed into the air or (2) the fragrance is evaporated into the air. Such volatile material dispensers generally include a housing with a refill inserted therein. The refill generally includes a container for holding a volatile material, wherein the volatile material may include various components including aroma chemicals, water, solvents, surfactants, alcohols, and other components. Some refills include a wick in contact with the volatile material and extending out of the refill to carry the volatile material out of the refill. Other refills include a gel-like substance that emits fragrance through a semi-permeable membrane. A refill may be inserted into a volatile material dispenser having a heater, a piezoelectric element, an aerosol actuator, a pump, or any other diffusion element that may assist in delivering the volatile material (or no diffusion element may be utilized). The water-based fragrance composition may be further diluted for use with some delivery systems. Regardless of the type of refill, consumers desire a longer lasting, more noticeable, and more consistent scent experience.

SUMMARY

According to one illustrative embodiment, a water-based fragrance composition may comprise at least about 67 wt % water and between about 5 and about 17 wt % of a first organic solvent, wherein the first organic solvent comprises one or more relatively volatile, water soluble, low molecular weight organic compound(s) having a boiling point less than about 100° C., wherein the relatively volatile, water soluble, low molecular weight organic compound(s) is selected from the group consisting of alcohols, ethers, ketones, esters (simple esters with a boiling point less than about 100° C.), or combinations thereof. The water-based fragrance composition may further include about 5 wt % or less of at least one fragrance formulation and between about 0 and about 22 wt % of a second organic solvent, wherein the second organic solvent comprises one or more moderately volatile, water soluble organic compound(s) having a boiling point greater than or equal to about 100° C. and less than or equal to about 300° C. The moderately volatile water soluble organic compound(s) is selected from the group consisting of polyhydric alcohols (including glycols), glycol ethers, glycol ether esters, sulfoxides, polyethers, lactones, carbonates, carboxylic acids, or combinations thereof.

In illustrative embodiments, the water-based fragrance composition and fragrance formulation ingredients may be free of any material with a boiling point greater than about 300 C.

In illustrative embodiments, the second organic solvent may be selected from the group consisting of dipropylene glycol methyl ether; propylene glycol methyl ether; dipropylene glycol; propylene glycol; pentylene glycol; caprylyl glycol; 1,2-hexanediol; propylene glycol methyl ether acetate; dipropylene glycol methyl ether acetate; propylene glycol monopropyl ether; ethylene glycol mono n-propyl ether; propylene glycol monoethyl ether; diethylene glycol monobutyl ether; ethylene glycol monohexyl ether; dimethoxymethane; dimethylsulfoxide, acetonitrile; and combinations thereof.

In illustrative embodiments, the second organic solvent may or may not be a volatile organic compound (VOC), or be VOC-exempt, as of the filing date of the present application.

In illustrative embodiments, the first organic solvent may be selected from the group consisting of: ethanol, isopropanol, acetone, or combinations thereof.

In illustrative embodiments, the water, the fragrance formulation, the first organic solvent, and the second organic solvent may form a homogenous liquid phase.

In illustrative embodiments, the water-based fragrance composition may comprise between about 0.05 and about 3 wt % of at least one fragrance formulation.

In illustrative embodiments, the water-based fragrance composition may comprise between about 10 and about 17 wt % of the first organic solvent.

In illustrative embodiments, the first organic solvent comprises ethanol and the second organic solvent may comprise dipropylene glycol methyl ether and dipropylene glycol.

In illustrative embodiments, the water-based fragrance composition may comprise about 67 wt % water, about 11 wt % ethanol, about 3 wt % fragrance formulation, about 6 wt % dipropylene glycol methyl ether, and about 10 wt % dipropylene glycol.

In illustrative embodiments, the first organic solvent may comprise ethanol and the second organic solvent may comprise dipropylene glycol methyl ether and 1,2-hexanediol.

In illustrative embodiments, the first organic solvent may comprise ethanol and the second organic solvent may comprise dipropylene glycol methyl ether and 1,2-hexanediol.

In illustrative embodiments, the water-based fragrance composition may comprise between about 4 wt % and about 9 wt % 1,2-hexanediol.

In illustrative embodiments, the water-based fragrance composition may comprise between about 4 wt % and about 9 wt % 1,2-hexanediol for a formula delivery or output rate of about 1 gram per hour. The amount of 1,2-hexanediol is adjusted accordingly if the delivery or output rate is changed.

According to another illustrative embodiment, a fragrance delivery device may comprise a reservoir for holding a liquid water-based fragrance composition, a wick extending into the reservoir and having a first end in contact with the liquid water-based fragrance composition, and a vibrating mesh nebulizer in contact with a second end of the wick. The wick may deliver the liquid water-based fragrance composition from the reservoir to the vibrating mesh nebulizer. The liquid water-based fragrance composition may comprise: a) at least about 67 wt % water; b) between about 5 and about 17 wt % of a first organic solvent, wherein the first organic solvent may comprise one or more relatively volatile, water soluble, low molecular weight organic compound(s) having a boiling point less than about 100° C., wherein the relatively volatile, water soluble, low molecular weight organic compound(s) is selected from the group consisting of alcohols, ethers, ketones, esters, and combinations thereof; c) about 5 wt % or less fragrance formulation; and d) between about 0 and about 22 wt % of a second organic solvent. The second organic solvent may comprise of one or more moderately volatile water soluble organic compound(s) having a boiling point greater than or equal to about 100° C. and less than or equal to about 300° C. The moderately volatile water soluble organic compound(s) may be selected from the group consisting of polyhydric alcohols (including glycols), glycol ethers, glycol ether esters, sulfoxides, ethers, polyethers, cyclic ethers, lactones, carbonates, carboxylic acid, and the like, or combinations thereof.

In illustrative embodiments, the nebulizer may convert the liquid water-based fragrance composition to droplets.

In illustrative embodiments, up to about 1 gram per hour of the water-based fragrance composition in the form of droplets may be delivered into the air by the vibrating mesh nebulizer.

In illustrative embodiments, up to about 2 grams per hour of the water-based fragrance composition in the form of droplets may be delivered into the air by the vibrating mesh nebulizer.

According to a further illustrative embodiment, a method of providing a long-lasting scent comprises the step of delivering boluses of droplets into air, wherein a vibrating mesh nebulizer converts a liquid water-based fragrance composition into the droplets. The liquid water-based fragrance composition may comprise: a) at least about 67 wt % water; b) between about 5 and about 17 wt % of a first organic solvent, wherein the first organic solvent comprises of one or more relatively volatile, water soluble, low molecular weight organic compound(s) having a boiling point less than about 100° C., wherein the relatively volatile, water soluble, low molecular weight organic compound(s) is selected from the group consisting of alcohols, ethers, ketones, esters, and combinations thereof; c) about 5 wt % or less fragrance; and d) between about 0 and about 22 wt % of a second organic solvent. The second organic solvent may comprise of one or more moderately volatile water soluble organic compound(s) having a boiling point greater than or equal to about 100° C. and less than or equal to about 300° C. The moderately volatile water soluble organic compound(s) may be selected from the group consisting of polyhydric alcohols (including glycols), glycol ethers, glycol ether esters, ethers, polyethers, cyclic ethers, lactones, carbonates, carboxylic acids, sulfoxides, and combinations thereof.

In illustrative embodiments, the water-based fragrance composition may be dispensed into the air by a volatile material dispenser. The volatile material dispenser may include a heater, a fan, a nebulizer, a trigger sprayer, or an aerosol dispenser.

In illustrative embodiments, the water-based fragrance composition may be free of antimicrobials.

In illustrative embodiments, the water-based fragrance composition may have a pH of between about 3 and about 10.

In illustrative embodiments, the water-based fragrance composition may include one or more pH adjuster.

BRIEF DESCRIPTION OF THE DRAWINGS

FIG. 1 is a top and front perspective view of an exemplary volatile material dispenser that may embody the principles of the present disclosure; and FIG. 2 is a cross-sectional view taken generally along the lines 2-2 of FIG. 1.

Other aspects and advantages of the present disclosure will become apparent upon consideration of the following detailed description, wherein similar structures have like or similar reference numerals.

DETAILED DESCRIPTION

The present disclosure is directed to water-based fragrance compositions, devices for emission of water-based fragrance compositions, and methods for emitting long-lasting scent. While the present disclosure may be embodied in many different forms, several specific embodiments are discussed herein with the understanding that the present disclosure is to be considered only as an exemplification of the principles of the disclosure, and it is not intended to limit the disclosure to the embodiments illustrated.

Referring to the drawings, FIGS. 1 and 2 depict a volatile material dispenser 50. The dispenser 50 may be adapted to accommodate a refill 52 (FIG. 2) and dispense a volatile material in the form of a water-based fragrance composition from the refill 52. The refill 52 may generally include a container 54 for holding the volatile material therein, wherein the container 54 is adapted to be retained within the dispenser 50. The container 54 may include a body 58 for holding the volatile material and a neck 60 extending outwardly from the body 58 and providing an opening into the container 54. A retaining mechanism 62 may be disposed within the neck 60 for holding a wick 64 with a first end of the wick 64 in contact with the volatile material and a second end of the wick 64 extending out of the container 54 through the neck 60. Although a particular dispenser 50 and a particular refill 52 are shown and described, it is contemplated that any type of dispenser and/or refill may be used with variations of the compositions described herein.

Referring to FIGS. 1 and 2, the dispenser 50 includes a housing 100 having an outlet channel 132 for volatilized water-based fragrance composition. The housing 100 encloses the refill 52 and electronic components of the dispenser 50. As best seen in FIG. 2, a printed circuit board (PCB) 160 or other control circuitry is supported within the housing 100 and a number of batteries 161 may be enclosed within a housing 100 and may be electrically connected to the PCB 160 for providing electrical power to the PCB 160 and/or other electrical components of the dispenser 50. The dispenser 50 may include one or more switches and/or buttons 172 operatively connected to the PCB 160 for turning the dispenser 50 on and off or altering any function of the dispenser 50, for example, an air flow generator speed, a volatile material emission rate, a boost of fragrance, or another other suitable function.

An optional air flow generator 200 may also be disposed within the housing 100 and electrically connected to the PCB 160 such that the PCB 160 may control operation of the air flow generator 200. A nebulizer assembly 248 may also be disposed within the housing 100 and may include a nebulizer. The nebulizer includes a piezoelectric element, which, in use, is positioned adjacent the wick 64 or other absorbent material extending from the refill 52 and in contact with the water-based fragrance composition to volatilize the water-based fragrance composition.

During operation, the nebulizer is actuated, either continuously or intermittently, to dispense the water-based fragrance composition. More particularly, an oscillating electric field is applied to the piezoelectric element, which causes expansion and contraction of the piezoelectric element in a radial direction. The expansion and contraction causes the orifice plate to vibrate in an axial direction (along a longitudinal axis of the dispenser 50), forcing the water-based fragrance composition retained within the orifices of the orifice plate away from the nebulizer and into the outlet manifold 130. The air flow generator 200 may also be actuated, either continuously or intermittently, the actuation of which may be coordinated in any suitable manner with operation of the nebulizer. The dispenser 50 is described in more detail in U.S. Application Ser. No. 61/992,027, filed on May 12, 2014, and entitled "Volatile Material Dispenser with Nebulizer and Nebulizer Assembly". While a particular volatile material dispenser is described and depicted herein, the water-based fragrance compositions may be dispensed from other volatile material dispensers using other actuation mechanisms (i.e. a heater, a fan, a nebulizer, an aerosol, a trigger sprayer, or any other suitable active or passive actuation mechanism) without departing from the scope of the present disclosure.

The volatile material disposed in the container 54 may be a water-based fragrance composition. In illustrative embodiments, the water-based fragrance composition includes water, first and second organic solvents, and one or more fragrance formulations. In illustrative embodiments, the water-based fragrance composition may include at least about 67 wt % water, between about 5 and about 17 wt % of the first organic solvent, between about 0 and about 22 wt % of the second organic solvent, and about 5 wt % or less of the one or more fragrances. In illustrative embodiments, the components of the water-based fragrance composition form a homogenous liquid phase.

Fragrances may be purchased from commercial vendors. Fragrances include one or more components. The components in fragrance may include one or more fragrance oils, surfactants, solvents, water, dyes, chlorophyll, stabilizers, emulsifiers, UV inhibitors, antioxidants, other additives, and/or any other suitable components. Fragrances, also called fragrance formulations herein, may have any of a wide variety of particular scents.

The first organic solvent is a component of the water-based fragrance composition that includes a relatively volatile, water soluble, low molecular weight organic compound or multiple such compounds. A compound is considered "water soluble" if a saturated solution of water includes at least 0.5 wt % of the compound. When calculating desirable ranges for the water-based fragrance composition, all of the relatively volatile, water soluble, low molecular weight organic compound or compounds present in the water-based fragrance composition are considered part of the first organic solvent. In illustrative embodiments, the first organic solvent may have a boiling point of less than about 100° C. Additionally, each of the relatively volatile, water soluble, low molecular weight organic compounds of the first organic solvent are defined as relatively volatile because each compound has a boiling point less than about 100° C. In illustrative embodiments, the first organic solvent may include one or more relatively volatile, water soluble, low molecular weight organic compounds selected from alcohols, ethers, ketones, esters, and the like, or combinations thereof.

In illustrative embodiments, the first organic solvent may or may not be volatile organic compounds (VOCs), as defined by California's Regulation for Consumer Products. As of this writing, an unofficial version of the Regulation for Consumer Products may be found at <http://www.arb.ca.gov/consprod/regs/2015/article_1_final_1-22-15.pdf>, definition (138). An official version may be found at <http://www.oal.ca.gov/CCR.htm>. The Regulation for Consumer Products defines a VOC as follows:

"Volatile Organic Compound (VOC)" means any compound containing at least one atom of carbon, excluding carbon monoxide, carbon dioxide, carbonic acid, metallic carbides or carbonates, and ammonium carbonate, and excluding the following:

(A) methane,
methylene chloride (dichloromethane),
1,1,1-trichloroethane (methyl chloroform),
trichlorofluoromethane (CFC-11),
dichlorodifluoromethane (CFC-12),
1,1,2-trichloro-1,2,2-trifluoroethane (CFC-113),
1,2-dichloro-1,1,2,2-tetrafluoroethane (CFC-114),
chloropentafluoroethane (CFC-115),
chlorodifluoromethane (HCFC-22),
1,1,1-trifluoro-2,2-dichloroethane (HCFC-123),
1,1-dichloro-1-fluoroethane (HCFC-141b),
1-chloro-1,1-difluoroethane (HCFC-142b),
2-chloro-1,1,1,2-tetrafluoroethane (HCFC-124),
trifluoromethane (HFC-23),
1,1,2,2-tetrafluoroethane (HFC-134),
1,1,1,2-tetrafluoroethane (HFC-134a),
pentafluoroethane (HFC-125),
1,1,1-trifluoroethane (HFC-143a),
1,1-difluoroethane (HFC-152a),
ethoxy-nonafluorobutane (HFE 7200),
trans-1,3,3,3-tetrafluoropropene (HFO-1234ze),
cyclic, branched, or linear completely methylated siloxanes,
the following classes of perfluorocarbons:
  1. cyclic, branched, or linear, completely fluorinated alkanes;
  2. cyclic, branched, or linear, completely fluorinated ethers with no unsaturations;
  3. cyclic, branched, or linear, completely fluorinated tertiary amines with no unsaturations; and
  4. sulfur-containing perfluorocarbons with no unsaturations and with the sulfur bonds to carbon and fluorine, and (B) the following low-reactive organic compounds which have been exempted by the U.S. EPA:
acetone,
ethane,
methyl acetate,
parachlorobenzotrifluoride (1-chloro-4-trifluoromethyl benzene),
perchloroethylene (tetrachloroethylene).

In other illustrative embodiments, the first organic solvent may include one or more VOCs, for example, ethanol or isopropanol.

In illustrative embodiments, the water-based fragrance composition may include between about 5 and about 17 wt % of the first organic solvent. In other illustrative embodiments, the water-based fragrance composition may include between about 10 and about 17 wt % of the first organic solvent. In other illustrative embodiments, the output rate of the water-based fragrance composition is about 1 gram per hour, the first organic solvent is ethanol, and the water-based fragrance composition may include between about 10 and about 11 wt % ethanol. In other illustrative embodiments, the output rate of the water-based fragrance composition is about 1 gram per hour, the first organic solvent is isopropanol, and the water-based fragrance composition may include about 5 wt % isopropanol. In other illustrative embodiments, the output rate of the water-based fragrance composition is about 1 gram per hour, the first organic solvent is acetone, and the water-based fragrance composition may include about 5 wt % acetone. In any of the preceding embodiments, the output rate of the water-based fragrance composition may alternatively be up to about 2 grams per hour.

The second organic solvent is a component of the water-based fragrance composition that includes a moderately volatile water soluble organic compound or multiple such compounds. When calculating desirable ranges for the water-based fragrance composition, all of the moderately volatile water soluble organic compound or compounds present in the water-based fragrance composition are considered part of the second organic solvent. In illustrative embodiments, the second organic solvent may have a boiling point greater than or equal to about 100° C. and less than or equal to about 300° C. Additionally, each of the moderately volatile water soluble organic compounds of the second organic solvent are defined as moderately volatile because each compound has a boiling point greater than or equal to about 100° C. and less than or equal to about 300° C.

In illustrative embodiments, the second organic solvent may be one or more moderately volatile water soluble organic compounds selected from polyhydric alcohols (including glycols), glycol ethers, glycol ether esters, sulfoxides, ethers, polyethers, cyclic ethers, lactones, carbonates, carboxylic acids, and the like, or combinations thereof. In illustrative embodiments, the second organic solvent may not be a VOC. In illustrative embodiments, the second organic solvent may include one or more of dipropylene glycol; propylene glycol; 1,2-hexanediol; dipropylene glycol methyl ether acetate; propylene glycol monopropyl ether; diethylene glycol monobutyl ether; or ethylene glycol monohexyl ether. In other illustrative embodiments, the second solvent may be a VOC, a non-VOC, or combinations thereof. Non-limiting examples of VOCs that are moderately volatile water soluble organic compounds include dipropylene glycol methyl ether; propylene glycol methyl ether; pentylene glycol; caprylyl glycol; propylene glycol methyl ether acetate; ethylene glycol mono n-propyl ether; propylene glycol monoethyl ether; dimethoxymethane; acetonitrile; dimethylsulfoxide; and combinations thereof. The current status of a solvent to determine whether or not it is a VOC should be checked and confirmed, as VOC lists change periodically, and no guarantees are made for the accuracy of the current VOC status as set by the California Environmental Protection Agency's Air Resources Board. In illustrative embodiments, the water-based fragrance composition includes between about 0 and about 22 wt % of the second organic solvent. In further illustrative embodiments, the water-based fragrance compositions includes between about 0 and about 17 wt % of the second organic solvent.

In illustrative embodiments, the water-based fragrance composition does not include a material with a boiling point greater than about 300° C. Solvents may be selected to solubilize 5 wt % or less of one or more fragrance without the inclusion of a material with a boiling point greater than about 300° C. In such embodiments, if the water-based fragrance composition includes more than one fragrance formulation, the total weight percentage of all fragrances is 5 wt % or less. In other illustrative embodiments, the solvents may be selected to solubilize 3 wt % or less of one or more fragrance formulations without the inclusion of any material with a boiling point greater than about 300° C. In such embodiments, if the water-based fragrance composition includes more than one fragrance, the total weight percentage of all the fragrance is about 3 wt % or less.

The components of the water-based fragrance composition may be selected with one or more of several goals in mind. The components may be selected for solubility. The water-based fragrance composition appears clear when a single, homogeneous phase is formed. When the water-based fragrance composition appears hazy or separates, the water-based fragrance composition did not fully solubilize the fragrance formulation. The clarity of the water-based fragrance composition may be checked at room temperature, or approximately 20° C. The clarity of the water-based fragrance composition may further be checked at 5° C. or −18° C. The components of the water-based fragrance composition may be selected for low surface tension to generate small droplets. The components of the water-based fragrance composition may additionally or alternatively be selected to achieve a higher flash point. In illustrative embodiments, the flashpoint may be greater than about 100° F. The components of the water-based fragrance composition may additionally or alternatively be selected to have a more mild or pleasant odor. The first and second organic solvents may be selected to minimize the presence of volatile organic compounds. For a given desired maximum output rate, the first and second organic solvents may be selected to meet the standards of California's Regulation for Consumer Products for the presence of specific volatile organic compounds.

The volatile material dispenser 50 nebulizes the water-based fragrance composition, delivering high intensity or noticeability of the fragrance formulation(s). By selecting a water-based fragrance composition with a low surface tension, droplet size is minimized. Further, smaller droplets prevent fallout or liquid accumulation of the volatile material around the volatile material dispenser 50. The resulting small droplets may be retained in the air for a longer period of time, thereby increasing noticeably and continuously filling a desired space with the water-based fragrance composition. Further, the volatile material dispenser 50 may be precisely controlled, for example, through the use of intensity controls, allowing a user to vary the amount of volatile material with high specificity. More particularly, a user may change, for example, a frequency at which the nebulizer is activated, a period of time during which the nebulizer is activated, a period of time between periods of activation (or dwell period), a speed of a fan (if present), one or more features or characteristics of the piezoelectric element and/or nebulizer, and/or any other suitable characteristics that would change emission of the nebulizer or other activation element (e.g., a fan). In illustrative embodiments, an output rate of the water-based fragrance composition may be about 1 gram per hour or up to about 1 gram per hour. In other illustrative embodiments, the output rate of the water-based fragrance composition may be about 2 grams per hour or up to about 2 grams per hour.

In an illustrative embodiment, the water-based fragrance composition comprises 11 wt % ethanol for the first organic solvent. Ethanol may be selected because it has a mild, agreeable odor, it may provide a fragrance lift, and it dissolves fragrance formulation components well by itself.

Ethanol has a high volatility. While including ethanol may lower the flash point, blending ethanol in the first organic solvent with, for example, dipropylene glycol methyl ether or propylene glycol methyl ether in the second organic solvent provides a synergy with a flash point higher than 100° F., a low solvent odor, and an optimal fragrance solubility up to about 5%.

In an illustrative embodiment, the second organic solvent comprises dipropylene glycol (DPG). DPG is characterized as odorless, has a low volatility, is not classified as a VOC, and aids in the solubility of fragrance formulation ingredients. In illustrative embodiments, the water-based fragrance composition may comprise between about 0 wt % and about 10 wt % of DPG. In other illustrative embodiments, the water-based fragrance composition may comprise between about 9 wt % and about 11 wt % of DPG. In a non-limiting, illustrative embodiment, the water-based fragrance composition comprises about 10 wt % of DPG.

In an illustrative embodiment, the second organic solvent comprises propylene glycol (PG). PG is characterized as odorless, has a low volatility, is not classified as a VOC, and aids in the solubility of fragrance formulations. In illustrative embodiments, the water-based fragrance composition may comprise between about 0 wt % and about 6 wt % of PG. In other illustrative embodiments, the water-based fragrance composition may comprise between about 2 wt % and about 6 wt % of PG. In a non-limiting, illustrative embodiment, the water-based fragrance composition comprises about 6 wt % of PG. In another non-limiting, illustrative embodiment, the water-based fragrance composition comprises about 4 wt % of PG. In yet another non-limiting, illustrative embodiment, the water-based fragrance composition comprises about 2 wt % of PG.

In another illustrative embodiment, the second organic solvent comprises 1,2-hexanediol. 1,2-hexanediol is characterized as odorless, has a low volatility, and is not classified as a VOC. The neighboring hydroxyl groups of 1,2-hexanediol create a head-tail polarity in the molecule. Consequently, 1,2-hexanediol has surfactant-like properties useful in the water-based fragrance composition. 1,2-hexanediol is an excellent co-solvent and can dissolve many fragrance formulations that other solvents cannot. In illustrative embodiments, the water-based fragrance composition may comprise between about 4 wt % and about 17 wt % 1,2-hexanediol. In other illustrative embodiments, the water-based fragrance composition may comprise between about 4 wt % and about 9 wt % 1,2-hexanediol. In still other embodiments, the water-based fragrance composition may comprise between about 5 wt % and about 7 wt % 1,2-hexanediol. In a non-limiting, illustrative embodiment, the water-based fragrance composition comprises about 9 wt % of 1,2-hexanediol.

In another illustrative embodiment, the second organic solvent comprises dipropylene glycol methyl ether acetate (DPMA). DPMA has a mild solvent odor, has a low volatility, is not classified as a VOC, and does not solubilize fragrance formulations on its own as well as in combination with DPG or PG. In illustrative embodiments, the water-based fragrance composition may comprise between about 0 wt % and about 6 wt % of DPMA. In other illustrative embodiments, the water-based fragrance composition may comprise between about 2 wt % and about 6 wt % of DPMA. In a non-limiting, illustrative embodiment, the water-based fragrance composition comprises about 6 wt % of DPMA. In another non-limiting, illustrative embodiment, the water-based fragrance composition comprises about 4 wt % of DPMA. In yet another non-limiting, illustrative embodiment, the water-based fragrance composition comprises about 2 wt % of DPMA.

In a further illustrative embodiment, the second organic solvent comprises propylene glycol methyl ether acetate (PMA). PMA has a chemical odor, is moderately volatile, and is classified as a VOC. A water-based fragrance composition that comprises ethanol and PMA has a slightly higher flashpoint than a water-based fragrance composition with ethanol alone (where the ethanol has the same total amount as the combination of ethanol and PMA) and has a high fragrance formulation solubility. Test data show that 3 wt % fragrance is soluble in a mixture of ethanol and PMA. In an illustrative embodiment, a water-based fragrance composition comprises water, one or more fragrance formulations, a first organic solvent comprising ethanol, and a second organic solvent comprising PMA and 1,2-hexanediol. In illustrative embodiments, the water-based fragrance composition may comprise between about 0 wt % and about 6 wt % of PMA. In other illustrative embodiments, the water-based fragrance composition may comprise between about 2 wt % and about 6 wt % of PMA. In a non-limiting, illustrative embodiment, the water-based fragrance composition comprises about 6 wt % of PMA. In another non-limiting, illustrative embodiment, the water-based fragrance composition comprises about 4 wt % of PMA. In yet another non-limiting, illustrative embodiment, the water-based fragrance composition comprises about 2 wt % of PMA.

In an illustrative embodiment, the second organic solvent comprises propylene glycol methyl ether (PM). PM is moderately volatile and is classified as a VOC. PM at about 17 wt % of a water-based fragrance composition does not dissolve fragrance formulations as well as fragrance compositions with ethanol alone or a blend of PMA and ethanol. A water-based fragrance composition that comprises ethanol and PM has a higher flashpoint than a water-based fragrance composition with ethanol alone (where the ethanol has the same total amount as the combination of ethanol and PM) and has a high fragrance formulation solubility. In an illustrative embodiment, a water-based fragrance composition comprises water, one or more fragrance formulation components, a first organic solvent comprising ethanol, and a second organic solvent comprising PM, wherein a concentration of ethanol is higher than a concentration of PM. In illustrative embodiments, the water-based fragrance composition may comprise between about 0 wt % and about 6 wt % of PM. In other illustrative embodiments, the water-based fragrance composition may comprise between about 2 wt % and about 6 wt % of PM. In a non-limiting, illustrative embodiment, the water-based fragrance composition comprises about 6 wt % of PM. In another non-limiting, illustrative embodiment, the water-based fragrance composition comprises about 4 wt % of PM. In yet another non-limiting, illustrative embodiment, the water-based fragrance composition comprises about 2 wt % of PM.

In an illustrative embodiment, the second organic solvent comprises dipropylene glycol methyl ether (DPM). DPM is moderately volatile and is classified as a VOC. DPM at about 17 wt % of a water-based fragrance composition does not dissolve fragrance formulations as well as fragrance compositions containing ethanol alone or a blend of PMA and ethanol. A water-based fragrance composition that comprises ethanol and DPM has a higher flashpoint than a water-based fragrance composition with ethanol alone (where the ethanol has the same total amount as the combination of ethanol and DPM) and has a high fragrance formulation solubility. In an illustrative embodiment, a water-based fragrance composition comprises water, one or more fragrance formulation components (up to about 5% fragrance formulation), a first organic solvent comprising ethanol, and a second organic solvent comprising DPM, wherein a concentration of ethanol is higher than a concentration of DPM. In illustrative embodiments, the water-based fragrance composition may comprise between about 0 wt % and about 6 wt % of DPM. In other illustrative embodiments, the water-based fragrance composition may comprise between about 2 wt % and about 6 wt % of DPM. In a non-limiting, illustrative embodiment, the water-based fragrance composition comprises about 2 wt % of DPM. In another non-limiting, illustrative embodiment, the water-based fragrance composition comprises about 4 wt % of DPM. In yet another non-limiting, illustrative embodiment, the water-based fragrance composition comprises about 2 wt % of DPM. In a non-limiting, illustrative embodiment, the water-based fragrance composition comprises about 6 wt % of DPM. In another non-limiting, illustrative embodiment, the water-based fragrance composition comprises between about 2 and about 6 wt % of DPM and about 9 wt % of 1,2-hexanediol. In another non-limiting, illustrative embodiment, the water-based fragrance composition comprises about 6 wt % of DPM and about 10 wt % of DPG.

The water-based fragrance formulations include at least one fragrance formulation component. A fragrance formulation may include, without limitation, at least twenty to fifty fragrance formulation components or perfume raw materials (PRM) and approximately 50% solvent system. In this art, the solvent system is free of surfactants or materials with a boiling point of greater than about 300 degrees C. At least one fragrance formulation may be selected based on certain properties, including without limitation, the estimated Log P of the components of that fragrance formulation, the range of chemistries and solubilities of the components of that fragrance formulation, the percent solids (using a residue of evaporations test or ROE), and the surface tension of one or more fragrance formulation components.

When the fragrance formulation is selected based on the estimated Log P of the components of that fragrance formulation, the estimated Log P may be determined in terms of $P_{OW}$ (octanol-water) and $P_{HW}$ (hexane-water). The Log $P_{OW}$ and Log $P_{HW}$ may be calculated for the individual fragrance formulation component or perfume raw material (PRM). The Log $P_{OW}$ is a standard quantity that is typically measured by pouring water and octanol together, putting some solute inside and determining the solute concentration in both phases. As the amount of solute is small, the concentrations of octanol and water are virtually unchanged. Therefore, Log P is generally a quantity which is always measured with the same two phases. Log P is a property of each PRM, but the whole mixture of PRMs (as in a fragrance formulation) will only dissolve if all PRMs are fully dissolved. The Log P of an individual PRM should not be the only factor used to get a fragrance property. The individual PRM Log P may be used to estimate the overall water solubility behavior of the fragrance, as well as the overall partitioning (or Log P) behavior of the fragrance. Determining the estimated Log P includes a partitioning that requires a two phase system, for example, the composition for the Log $P_{OW}$ may include a water phase of nearly 100% water and an octanol phase of 27.4 mol % water and 72.6 mol % octanol. The composition for the Log $P_{HW}$ may include a water phase of nearly 100% water and a hexane phase of nearly 100% hexane. In one embodiment, at least one fragrance formulation includes one or more fragrance formulation components having an estimated Log P with a Log $P_{OW}$ of less than 2.0 and a Log $P_{HW}$ of less than 1.0, and may include a solubility of greater than 5%. The Log P and solubility values were estimated using COSMOtherm version 1501, parameterization BP_TZVPD_FINE_C30_1501. The molecules were calculated with TURBOMOLE 6.6 and COSMOconf 3.0.

In one embodiment, the water-based fragrance composition may include at least one fragrance formulation that includes at least one fragrance formulation component with an estimated Log P with a Log $P_{OW}$ of less than 2.0 and a Log $P_{HW}$ of less than 1.0, a solubility greater than 5%, and is clear at approximately 20° C. Fragrance formulation components with such properties may include, without limitation, coumarin, ethyl vanillin, cinnamic alcohol, cinnamic aldehyde, phenylethyl alcohol, vanillin, fructone and gamma-hexalactone. The Log P values listed below would be the same for all solvent formulas and examples listed in this art, but the specific solubility values would change for different formulas. However, the Log P and solubilities will generally correlate as long as the formula is water dominated. The correlation will break down for other solvents (ethanol, propylene glycol, etc.). The solubilities listed in the example below are specific to Example 5. The Log P and solubility values listed in the table below were estimated from COSMOtherm version 1501, parameterization BP_TZVPD_FINE_C30_1501. The molecules were calculated with TURBOMOLE 6.6 and COSMOconf 3.0.

Table 1 below is a list of exemplary fragrance formulation components and properties of those components, wherein each of the fragrance formulation components has a Log $P_{OW}$ of less than 2.0 and a Log $P_{HW}$ of less than 1.0.

TABLE 1

| Perfume Raw Material | CAS | $LogP_{OW}$ | $LogP_{HW}$ | Solubility | Solubility in % |
|---|---|---|---|---|---|
| COUMARIN | 91-64-5 | 1.29 | 0.11 | 0.05399 | 5.39876 |
| ETHYL VANILLIN | 121-32-4 | 1.70 | 0.19 | 0.05578 | 5.57779 |
| CINNAMIC ALCOHOL | 104-54-1 | 1.93 | 0.23 | 0.05695 | 5.69483 |
| CINNAMIC ALDEHYDE | 104-55-2 | 1.49 | 0.44 | 0.06415 | 6.41523 |
| PHENYLETHYL ALCOHOL | 60-12-8 | 1.61 | −0.06 | 0.08916 | 8.91553 |
| VANILLIN | 121-33-5 | 1.19 | −0.65 | 0.12157 | 12.15747 |
| FRUCTONE | 6413-10-1 | 1.19 | 0.51 | 0.12853 | 12.85252 |
| GAMMA-HEXALACTONE | 695-06-7 | 0.53 | −0.61 | 0.32566 | 32.56558 |

Additional embodiments of water-based fragrance compositions are described in the following examples. The examples are meant to be illustrative and not to be limiting. Each example includes the composition of the water-based fragrance composition separated by component. Each example also includes some of the properties of the water-based fragrance composition when measured Examples 1-22 include the flashpoint, VOC content, and Refractive Index @20° C. for the example water-based fragrance composition. Each of these examples further includes a visual test of the water-based fragrance composition at room temperature and 5° C. The water-based fragrance composition fully solubilized the fragrance formulation if it appears clear. The VOC content in all of the following charts refers to the VOC content without the inclusion of VOC's within the fragrance, which may be about 1% VOC additional to the water-based fragrance formulation.

Example 1

| | SCJ1 52874 | |
|---|---|---|
| Water | Deionized (DI) water | 70 wt % |
| Fragrance formulation | Fragrance #1 | 3 wt % |
| First Organic Solvent | Ethanol | 17 wt % |
| Second Organic Solvent | Dipropylene glycol | 10 wt % |
| Properties | Flashpoint (° F.) | 91.4° F. |
| | VOC Content (wt %) (without fragrance) | 17 wt % |
| | Refractive Index @ 20° C. | 1.36 |
| | Solubility, RT | Clear |
| | Solubility, 5° C. | Clear |

Example 2

| | SCJ1 Mod PMA1 | |
|---|---|---|
| Water | DI water | 70 wt % |
| Fragrance formulation | Fragrance #1 | 3 wt % |
| First Organic Solvent | Ethanol | 11 wt % |
| Second Organic Solvent | Propylene Glycol Methyl Ether Acetate | 6 wt % |
| | Dipropylene glycol | 10 wt % |
| Properties | Flashpoint (° F.) | 100.4° F. |
| | VOC Content (wt %) (without fragrance) | 17 wt % |
| | Refractive Index @ 20° C. | 1.36 |
| | Solubility, RT | Clear |
| | Solubility, 5° C. | Clear |

Example 3

| | SCJ1 Mod PMA2 | |
|---|---|---|
| Water | DI water | 70 wt % |
| Fragrance formulation | Fragrance #1 | 3 wt % |
| First Organic Solvent | Ethanol | 13 wt % |
| Second Organic Solvent | Propylene Glycol Methyl Ether Acetate | 4 wt % |
| | Dipropylene glycol | 10 wt % |
| Properties | Flashpoint (° F.) | 96.8° F. |
| | VOC Content (wt %) (without fragrance) | 17 wt % |
| | Refractive Index @ 20° C. | 1.36 |
| | Solubility, RT | Clear |
| | Solubility, 5° C. | Clear |

Example 4

| | SCJ1 Mod PMA3 | |
|---|---|---|
| Water | DI water | 70 wt % |
| Fragrance formulation | Fragrance #1 | 3 wt % |
| First Organic Solvent | Ethanol | 15 wt % |
| Second Organic Solvent | Propylene Glycol Methyl Ether Acetate | 2 wt % |
| | Dipropylene glycol | 10 wt % |
| Properties | Flashpoint (° F.) | 96.8° F. |
| | VOC Content (wt %) (without fragrance) | 17 wt % |
| | Refractive Index @ 20° C. | 1.36 |
| | Solubility, RT | Clear |
| | Solubility, 5° C. | Clear |

Example 5

| | SCJ1 Mod DPM1 | |
|---|---|---|
| Water | DI water | 70 wt % |
| Fragrance formulation | Fragrance #1 | 3 wt % |
| First Organic Solvent | Ethanol | 11 wt % |
| Second Organic Solvent | DiPropylene Glycol Methyl Ether | 6 wt % |
| | Dipropylene glycol | 10 wt % |
| Properties | Flashpoint (° F.) | 104° F. |
| | VOC Content (wt %) (without fragrance) | 17 wt % |
| | Refractive Index @ 20° C. | 1.36 |
| | Solubility, RT | Clear |
| | Solubility, 5° C. | Clear |

Example 6

| | SCJ1 Mod DPM2 | |
|---|---|---|
| Water | DI water | 70 wt % |
| Fragrance formulation | Fragrance #1 | 3 wt % |
| First Organic Solvent | Ethanol | 13 wt % |
| Second Organic Solvent | DiPropylene Glycol Methyl Ether | 4 wt % |
| | Dipropylene glycol | 10 wt % |
| Properties | Flashpoint (° F.) | 96.8° F. |
| | VOC Content (wt %) (without fragrance) | 17 wt % |
| | Refractive Index @ 20° C. | 1.36 |
| | Solubility, RT | Clear |
| | Solubility, 5° C. | Clear |

Example 7

| | SCJ1 Mod DPM3 | |
|---|---|---|
| Water | DI water | 70 wt % |
| Fragrance formulation | Fragrance #1 | 3 wt % |
| First Organic Solvent | Ethanol | 15 wt % |
| Second Organic Solvent | DiPropylene Glycol Methyl Ether | 2 wt % |
| | Dipropylene glycol | 10 wt % |
| Properties | Flashpoint (° F.) | 96.8° F. |
| | VOC Content (wt %) (without fragrance) | 17 wt % |

SCJ1 Mod DPM3

| | | |
|---|---|---|
| Refractive Index @ 20° C. | 1.36 | |
| Solubility, RT | Clear | |
| Solubility, 5° C. | Clear | |

Example 8

SCJ1 Mod PM1

| | | |
|---|---|---|
| Water | DI water | 70 wt % |
| Fragrance formulation | Fragrance #1 | 3 wt % |
| First Organic Solvent | Ethanol | 11 wt % |
| Second Organic Solvent | Propylene Glycol Methyl Ether | 6 wt % |
| | Dipropylene glycol | 10 wt % |
| Properties | Flashpoint (° F.) | 104° F. |
| | VOC Content (wt %) (without fragrance) | 17 wt % |
| | Refractive Index @ 20° C. | 1.36 |
| | Solubility, RT | Clear |
| | Solubility, 5° C. | Clear |

Example 9

SCJ1 Mod PM2

| | | |
|---|---|---|
| Water | DI water | 70 wt % |
| Fragrance formulation | Fragrance #1 | 3 wt % |
| First Organic Solvent | Ethanol | 13 wt % |
| Second Organic Solvent | Propylene Glycol Methyl Ether | 4 wt % |
| | Dipropylene glycol | 10 wt % |
| Properties | Flashpoint (° F.) | 100.4° F. |
| | VOC Content (wt %) (without fragrance) | 17 wt % |
| | Refractive Index @ 20° C. | 1.36 |
| | Solubility, RT | Clear |
| | Solubility, 5° C. | Clear |

Example 10

SCJ1 Mod PM3

| | | |
|---|---|---|
| Water | DI water | 70 wt % |
| Fragrance formulation | Fragrance #1 | 3 wt % |
| First Organic Solvent | Ethanol | 15 wt % |
| Second Organic Solvent | Propylene Glycol Methyl Ether | 2 wt % |
| | Dipropylene glycol | 10 wt % |
| Properties | Flashpoint (° F.) | 96.8° F. |
| | VOC Content (wt %) (without fragrance) | 17 wt % |
| | Refractive Index @ 20° C. | 1.36 |
| | Solubility, RT | Clear |
| | Solubility, 5° C. | Clear |

Example 11

SCJ3 Mod PMA1

| | | |
|---|---|---|
| Water | DI water | 71 wt % |
| Fragrance formulation | Fragrance #1 | 3 wt % |
| First Organic Solvent | Ethanol | 11 wt % |
| Second Organic Solvent | Propylene Glycol Methyl Ether Acetate | 6 wt % |
| | 1,2-hexanediol | 9 wt % |
| Properties | Flashpoint (° F.) | 107.6° F. |
| | VOC Content (wt %) (without fragrance) | 17 wt % |
| | Refractive Index @ 20° C. | 1.36 |
| | Solubility, RT | Clear |
| | Solubility, 5° C. | Clear |

Example 12

SCJ3 Mod PMA2

| | | |
|---|---|---|
| Water | DI water | 71 wt % |
| Fragrance formulation | Fragrance #1 | 3 wt % |
| First Organic Solvent | Ethanol | 13 wt % |
| Second Organic Solvent | Propylene Glycol Methyl Ether Acetate | 4 wt % |
| | 1,2-hexanediol | 9 wt % |
| Properties | Flashpoint (° F.) | 104° F. |
| | VOC Content (wt %) (without fragrance) | 17 wt % |
| | Refractive Index @ 20° C. | 1.36 |
| | Solubility, RT | Clear |
| | Solubility, 5° C. | Clear |

Example 13

SCJ3 Mod PMA3

| | | |
|---|---|---|
| Water | DI water | 71 wt % |
| Fragrance formulation | Fragrance #1 | 3 wt % |
| First Organic Solvent | Ethanol | 15 wt % |
| Second Organic Solvent | Propylene Glycol Methyl Ether Acetate | 2 wt % |
| | 1,2-hexanediol | 9 wt % |
| Properties | Flashpoint (° F.) | 100.4° F. |
| | VOC Content (wt %) (without fragrance) | 17 wt % |
| | Refractive Index @ 20° C. | 1.36 |
| | Solubility, RT | Clear |
| | Solubility, 5° C. | Clear |

Example 14

SCJ3 Mod DPM1

| | | |
|---|---|---|
| Water | DI water | 71 wt % |
| Fragrance formulation | Fragrance #1 | 3 wt % |
| First Organic Solvent | Ethanol | 11 wt % |
| Second Organic Solvent | DiPropylene Glycol Methyl Ether | 6 wt % |
| | 1,2-hexanediol | 9 wt % |
| Properties | Flashpoint (° F.) | 111.2° F. |
| | VOC Content (wt %) (without fragrance) | 17 wt % |

SCJ3 Mod DPM1

| | | |
|---|---|---|
| | Refractive Index @ 20° C. | 1.36 |
| | Solubility, RT | Clear |
| | Solubility, 5° C. | Clear |

Example 15

SCJ3 Mod DPM2

| | | |
|---|---|---|
| Water | DI water | 71 wt % |
| Fragrance formulation | Fragrance #1 | 3 wt % |
| First Organic Solvent | Ethanol | 13 wt % |
| Second Organic Solvent | DiPropylene Glycol Methyl Ether | 4 wt % |
| | 1,2-hexanediol | 9 wt % |
| Properties | Flashpoint (° F.) | 107.6° F. |
| | VOC Content (wt %) (without fragrance) | 17 wt % |
| | Refractive Index @ 20° C. | 1.36 |
| | Solubility, RT | Clear |
| | Solubility, 5° C. | Clear |

Example 16

SCJ3 Mod DPM3

| | | |
|---|---|---|
| Water | DI water | 71 wt % |
| Fragrance formulation | Fragrance #1 | 3 wt % |
| First Organic Solvent | Ethanol | 15 wt % |
| Second Organic Solvent | DiPropylene Glycol Methyl Ether | 2 wt % |
| | 1,2-hexanediol | 9 wt % |
| Properties | Flashpoint (° F.) | 104° F. |
| | VOC Content (wt %) (without fragrance) | 17 wt % |
| | Refractive Index @ 20° C. | 1.36 |
| | Solubility, RT | Clear |
| | Solubility, 5° C. | Clear |

Example 17

SCJ3 Mod hex1

| | | |
|---|---|---|
| Water | DI water | 77 wt % |
| Fragrance formulation | Fragrance #1 | 3 wt % |
| First Organic Solvent | Ethanol | 13 wt % |
| Second Organic Solvent | 1,2-hexanediol | 7 wt % |
| Properties | Flashpoint (° F.) | 104° F. |
| | VOC Content (wt %) (without fragrance) | 13 wt % |
| | Refractive Index @ 20° C. | 1.35 |
| | Solubility, RT | Clear |
| | Solubility, 5° C. | Clear |

Example 18

SCJ3 Mod hex2

| | | |
|---|---|---|
| Water | DI water | 79 wt % |
| Fragrance formulation | Fragrance #1 | 3 wt % |
| First Organic Solvent | Ethanol | 13 wt % |
| Second Organic Solvent | 1,2-hexanediol | 5 wt % |
| Properties | Flashpoint (° F.) | 104° F. |
| | VOC Content (wt %) (without fragrance) | 13 wt % |
| | Refractive Index @ 20° C. | 1.35 |
| | Solubility, RT | Clear |
| | Solubility, 5° C. | Clear |

Example 19

SCJ3 Mod PM1

| | | |
|---|---|---|
| Water | DI water | 71 wt % |
| Fragrance formulation | Fragrance #1 | 3 wt % |
| First Organic Solvent | Ethanol | 11 wt % |
| Second Organic Solvent | PM | 6 wt % |
| | 1,2-hexanediol | 9 wt % |
| Properties | Flashpoint (° F.) | 111.2° F. |
| | VOC Content (wt %) (without fragrance) | 17 wt % |
| | Refractive Index @ 20° C. | 1.36 |
| | Solubility, RT | Clear |
| | Solubility, 5° C. | Clear |

Example 20

SCJ3 Mod PM2

| | | |
|---|---|---|
| Water | DI water | 71 wt % |
| Fragrance formulation | Fragrance #1 | 3 wt % |
| First Organic Solvent | Ethanol | 13 wt % |
| Second Organic Solvent | Propylene Glycol Methyl Ether | 4 wt % |
| | 1,2-hexanediol | 9 wt % |
| Properties | Flashpoint (° F.) | 107.6° F. |
| | VOC Content (wt %) (without fragrance) | 17 wt % |
| | Refractive Index @ 20° C. | 1.36 |
| | Solubility, RT | Clear |
| | Solubility, 5° C. | Clear |

Example 21

SCJ3 Mod PM3

| | | |
|---|---|---|
| Water | DI water | 71 wt % |
| Fragrance formulation | Fragrance #1 | 3 wt % |
| First Organic Solvent | Ethanol | 15 wt % |
| Second Organic Solvent | Propylene Glycol Methyl Ether | 2 wt % |
| | 1,2-hexanediol | 9 wt % |
| Properties | Flashpoint (° F.) | 104° F. |
| | VOC Content (wt %) (without fragrance) | 17 wt % |
| | Refractive Index @ 20° C. | 1.36 |
| | Solubility, RT | Clear |
| | Solubility, 5° C. | Clear |

Examples 22-81 include a visual test of the water-based fragrance composition at room temperature and 5° C. The water-based fragrance composition fully solubilized the fragrance formulation if it appears clear.

Example 22

| SCJ1 - Fragrance #2 | | |
|---|---|---|
| Water | Deionized (DI) water | 70 wt % |
| Fragrance formulation | Fragrance #2 | 3 wt % |
| First Organic Solvent | Ethanol | 17 wt % |
| Second Organic Solvent | Dipropylene glycol | 10 wt % |
| Properties | VOC Content (wt %) (without fragrance) | 17 wt % |
| | Solubility, RT | Clear |
| | Solubility, 5° C. | Clear |

Example 23

| SCJ1 Mod PMA1 | | |
|---|---|---|
| Water | DI water | 70 wt % |
| Fragrance formulation | Fragrance #2 | 3 wt % |
| First Organic Solvent | Ethanol | 11 wt % |
| Second Organic Solvent | Propylene Glycol Methyl Ether Acetate | 6 wt % |
| | Dipropylene glycol | 10 wt % |
| Properties | VOC Content (wt %) (without fragrance) | 17 wt % |
| | Solubility, RT | Clear |
| | Solubility, 5° C. | Clear |

Example 24

| SCJ1 Mod DPM1 | | |
|---|---|---|
| Water | DI water | 70 wt % |
| Fragrance formulation | Fragrance #2 | 3 wt % |
| First Organic Solvent | Ethanol | 11 wt % |
| Second Organic Solvent | DiPropylene Glycol Methyl Ether | 6 wt % |
| | Dipropylene glycol | 10 wt % |
| Properties | VOC Content (wt %) (without fragrance) | 17 wt % |
| | Solubility, RT | Clear |
| | Solubility, 5° C. | Clear |

Example 25

| SCJ1 Mod PM1 | | |
|---|---|---|
| Water | DI water | 70 wt % |
| Fragrance formulation | Fragrance #2 | 3 wt % |
| First Organic Solvent | Ethanol | 11 wt % |
| Second Organic Solvent | Propylene Glycol Methyl Ether | 6 wt % |
| | Dipropylene glycol | 10 wt % |
| Properties | VOC Content (wt %) (without fragrance) | 17 wt % |
| | Solubility, RT | Clear |
| | Solubility, 5° C. | Clear |

Example 26

| SCJ3 Mod PMA1 | | |
|---|---|---|
| Water | DI water | 71 wt % |
| Fragrance formulation | Fragrance #2 | 3 wt % |
| First Organic Solvent | Ethanol | 11 wt % |
| Second Organic Solvent | Propylene Glycol Methyl Ether Acetate | 6 wt % |
| | 1,2-hexanediol | 9 wt % |
| Properties | VOC Content (wt %) (without fragrance) | 17 wt % |
| | Solubility, RT | Clear |
| | Solubility, 5° C. | Clear |

Example 27

| SCJ3 Mod DPM1 | | |
|---|---|---|
| Water | DI water | 71 wt % |
| Fragrance formulation | Fragrance #2 | 3 wt % |
| First Organic Solvent | Ethanol | 11 wt % |
| Second Organic Solvent | DiPropylene Glycol Methyl Ether | 6 wt % |
| | 1,2-hexanediol | 9 wt % |
| Properties | VOC Content (wt %) (without fragrance) | 17 wt % |
| | Solubility, RT | Clear |
| | Solubility, 5° C. | Clear |

Example 28

| SCJ3 Mod hex1 | | |
|---|---|---|
| Water | DI water | 77 wt % |
| Fragrance formulation | Fragrance #2 | 3 wt % |
| First Organic Solvent | Ethanol | 13 wt % |
| Second Organic Solvent | 1,2-hexanediol | 7 wt % |
| Properties | VOC Content (wt %) (without fragrance) | 13 wt % |
| | Solubility, RT | Clear |
| | Solubility, 5° C. | Clear |

Example 29

| SCJ3 Mod hex2 | | |
|---|---|---|
| Water | DI water | 79 wt % |
| Fragrance formulation | Fragrance #2 | 3 wt % |
| First Organic Solvent | Ethanol | 13 wt % |
| Second Organic Solvent | 1,2-hexanediol | 5 wt % |
| Properties | VOC Content (wt %) (without fragrance) | 13 wt % |
| | Solubility, RT | Clear |
| | Solubility, 5° C. | Clear |

Example 30

| SCJ3 Mod PM1 | | |
|---|---|---|
| Water | DI water | 71 wt % |
| Fragrance formulation | Fragrance #2 | 3 wt % |
| First Organic Solvent | Ethanol | 11 wt % |

SCJ3 Mod PM1

| | | |
|---|---|---|
| Second Organic Solvent | Propylene Glycol Methyl Ether | 6 wt % |
| | 1,2-hexanediol | 9 wt % |
| Properties | VOC Content (wt %) (without fragrance) | 17 wt % |
| | Solubility, RT | Clear |
| | Solubility, 5° C. | Clear |

Example 31

SCJ1 - Fragrance #3

| | | |
|---|---|---|
| Water | Deionized (DI) water | 70 wt % |
| Fragrance formulation | Fragrance #3 | 3 wt % |
| First Organic Solvent | Ethanol | 17 wt % |
| Second Organic Solvent | Dipropylene glycol | 10 wt % |
| Properties | VOC Content (wt %) (without fragrance) | 17 wt % |
| | Solubility, RT | Clear |
| | Solubility, 5° C. | Clear |

Example 32

SCJ1 Mod PMA1

| | | |
|---|---|---|
| Water | DI water | 70 wt % |
| Fragrance formulation | Fragrance #3 | 3 wt % |
| First Organic Solvent | Ethanol | 11 wt % |
| Second Organic Solvent | Propylene Glycol Methyl Ether Acetate | 6 wt % |
| | Dipropylene glycol | 10 wt % |
| Properties | VOC Content (wt %) (without fragrance) | 17 wt % |
| | Solubility, RT | Clear |
| | Solubility, 5° C. | Clear |

Example 33

SCJ1 Mod DPM1

| | | |
|---|---|---|
| Water | DI water | 70 wt % |
| Fragrance formulation | Fragrance #3 | 3 wt % |
| First Organic Solvent | Ethanol | 11 wt % |
| Second Organic Solvent | DiPropylene Glycol Methyl Ether | 6 wt % |
| | Dipropylene glycol | 10 wt % |
| Properties | VOC Content (wt %) (without fragrance) | 17 wt % |
| | Solubility, RT | Clear |
| | Solubility, 5° C. | Clear |

Example 34

SCJ1 Mod PM1

| | | |
|---|---|---|
| Water | DI water | 70 wt % |
| Fragrance formulation | Fragrance #3 | 3 wt % |
| First Organic Solvent | Ethanol | 11 wt % |

SCJ1 Mod PM1

| | | |
|---|---|---|
| Second Organic Solvent | Propylene Glycol Methyl Ether | 6 wt % |
| | Dipropylene glycol | 10 wt % |
| Properties | VOC Content (wt %) (without fragrance) | 17 wt % |
| | Solubility, RT | Clear |
| | Solubility, 5° C. | Clear |

Example 35

SCJ3 Mod PMA1

| | | |
|---|---|---|
| Water | DI water | 71 wt % |
| Fragrance formulation | Fragrance #3 | 3 wt % |
| First Organic Solvent | Ethanol | 11 wt % |
| Second Organic Solvent | Propylene Glycol Methyl Ether Acetate | 6 wt % |
| | 1,2-hexanediol | 9 wt % |
| Properties | VOC Content (wt %) (without fragrance) | 17 wt % |
| | Solubility, RT | Clear |
| | Solubility, 5° C. | Clear |

Example 36

SCJ3 Mod DPM1

| | | |
|---|---|---|
| Water | DI water | 71 wt % |
| Fragrance formulation | Fragrance #3 | 3 wt % |
| First Organic Solvent | Ethanol | 11 wt % |
| Second Organic Solvent | DiPropylene Glycol Methyl Ether | 6 wt % |
| | 1,2-hexanediol | 9 wt % |
| Properties | VOC Content (wt %) (without fragrance) | 17 wt % |
| | Solubility, RT | Clear |
| | Solubility, 5° C. | Clear |

Example 37

SCJ3 Mod hex1

| | | |
|---|---|---|
| Water | DI water | 77 wt % |
| Fragrance formulation | Fragrance #3 | 3 wt % |
| First Organic Solvent | Ethanol | 13 wt % |
| Second Organic Solvent | 1,2-hexanediol | 7 wt % |
| Properties | VOC Content (wt %) (without fragrance) | 13 wt % |
| | Solubility, RT | Clear |
| | Solubility, 5° C. | Clear |

Example 38

SCJ3 Mod hex2

| | | |
|---|---|---|
| Water | DI water | 79 wt % |
| Fragrance formulation | Fragrance #3 | 3 wt % |
| First Organic Solvent | Ethanol | 13 wt % |

SCJ3 Mod hex2

| | | |
|---|---|---|
| Second Organic Solvent | 1,2-hexanediol | 5 wt % |
| Properties | VOC Content (wt %) (without fragrance) | 13 wt % |
| | Solubility, RT | Clear |
| | Solubility, 5° C. | Clear |

Example 39

SCJ3 Mod PM1

| | | |
|---|---|---|
| Water | DI water | 71 wt % |
| Fragrance formulation | Fragrance #3 | 3 wt % |
| First Organic Solvent | Ethanol | 11 wt % |
| Second Organic Solvent | Propylene Glycol Methyl Ether | 6 wt % |
| | 1,2-hexanediol | 9 wt % |
| Properties | VOC Content (wt %) (without fragrance) | 17 wt % |
| | Solubility, RT | Clear |
| | Solubility, 5° C. | Clear |

Example 40

SCJ1 - Fragrance #4

| | | |
|---|---|---|
| Water | Deionized (DI) water | 70 wt % |
| Fragrance formulation | Fragrance #4 | 3 wt % |
| First Organic Solvent | Ethanol | 17 wt % |
| Second Organic Solvent | Dipropylene glycol | 10 wt % |
| Properties | VOC Content (wt %) (without fragrance) | 17 wt % |
| | Solubility, RT | Clear |
| | Solubility, 5° C. | Clear |

Example 41

SCJ1 Mod DPM1

| | | |
|---|---|---|
| Water | DI water | 70 wt % |
| Fragrance formulation | Fragrance #4 | 3 wt % |
| First Organic Solvent | Ethanol | 11 wt % |
| Second Organic Solvent | DiPropylene Glycol Methyl Ether | 6 wt % |
| | Dipropylene glycol | 10 wt % |
| Properties | VOC Content (wt %) (without fragrance) | 17 wt % |
| | Solubility, RT | Clear |
| | Solubility, 5° C. | Clear |

Example 42

SCJ1 Mod PM1

| | | |
|---|---|---|
| Water | DI water | 70 wt % |
| Fragrance formulation | Fragrance #4 | 3 wt % |
| First Organic Solvent | Ethanol | 11 wt % |

SCJ1 Mod PM1

| | | |
|---|---|---|
| Second Organic Solvent | Propylene Glycol Methyl Ether | 6 wt % |
| | Dipropylene glycol | 10 wt % |
| Properties | VOC Content (wt %) (without fragrance) | 17 wt % |
| | Solubility, RT | Clear |
| | Solubility, 5° C. | Clear |

Example 43

SCJ3 Mod PMA1

| | | |
|---|---|---|
| Water | DI water | 71 wt % |
| Fragrance formulation | Fragrance #4 | 3 wt % |
| First Organic Solvent | Ethanol | 11 wt % |
| Second Organic Solvent | Propylene Glycol Methyl Ether Acetate | 6 wt % |
| | 1,2-hexanediol | 9 wt % |
| Properties | VOC Content (wt %) (without fragrance) | 17 wt % |
| | Solubility, RT | Clear |
| | Solubility, 5° C. | Clear |

Example 44

SCJ3 Mod DPM1

| | | |
|---|---|---|
| Water | DI water | 71 wt % |
| Fragrance formulation | Fragrance #4 | 3 wt % |
| First Organic Solvent | Ethanol | 11 wt % |
| Second Organic Solvent | DiPropylene Glycol Methyl Ether | 6 wt % |
| | 1,2-hexanediol | 9 wt % |
| Properties | VOC Content (wt %) (without fragrance) | 17 wt % |
| | Solubility, RT | Clear |
| | Solubility, 5° C. | Clear |

Example 45

SCJ3 Mod hex1

| | | |
|---|---|---|
| Water | DI water | 77 wt % |
| Fragrance formulation | Fragrance #4 | 3 wt % |
| First Organic Solvent | Ethanol | 13 wt % |
| Second Organic Solvent | 1,2-hexanediol | 7 wt % |
| Properties | VOC Content (wt %) (without fragrance) | 13 wt % |
| | Solubility, RT | Clear |
| | Solubility, 5° C. | Clear |

Example 46

SCJ3 Mod hex2

| | | |
|---|---|---|
| Water | DI water | 79 wt % |
| Fragrance formulation | Fragrance #4 | 3 wt % |
| First Organic Solvent | Ethanol | 13 wt % |

SCJ3 Mod hex2

| | | |
|---|---|---|
| Second Organic Solvent | 1,2-hexanediol | 5 wt % |
| Properties | VOC Content (wt %) (without fragrance) | 13 wt % |
| | Solubility, RT | Clear |
| | Solubility, 5° C. | Clear |

Example 47

SCJ3 Mod PM1

| | | |
|---|---|---|
| Water | DI water | 71 wt % |
| Fragrance formulation | Fragrance #4 | 3 wt % |
| First Organic Solvent | Ethanol | 11 wt % |
| Second Organic Solvent | Propylene Glycol Methyl Ether | 6 wt % |
| | 1,2-hexanediol | 9 wt % |
| Properties | VOC Content (wt %) (without fragrance) | 17 wt % |
| | Solubility, RT | Clear |
| | Solubility, 5° C. | Clear |

Example 48

SCJ3 Mod PMA1

| | | |
|---|---|---|
| Water | DI water | 71 wt % |
| Fragrance formulation | Fragrance #5 | 3 wt % |
| First Organic Solvent | Ethanol | 11 wt % |
| Second Organic Solvent | Propylene Glycol Methyl Ether Acetate | 6 wt % |
| | 1,2-hexanediol | 9 wt % |
| Properties | VOC Content (wt %) (without fragrance) | 17 wt % |
| | Solubility, RT | Clear |
| | Solubility, 5° C. | Clear |

Example 49

SCJ3 Mod DPM1

| | | |
|---|---|---|
| Water | DI water | 71 wt % |
| Fragrance formulation | Fragrance #5 | 3 wt % |
| First Organic Solvent | Ethanol | 11 wt % |
| Second Organic Solvent | DiPropylene Glycol Methyl Ether | 6 wt % |
| | 1,2-hexanediol | 9 wt % |
| Properties | VOC Content (wt %) (without fragrance) | 17 wt % |
| | Solubility, RT | Clear |
| | Solubility, 5° C. | Clear |

Example 50

SCJ3 Mod hex1

| | | |
|---|---|---|
| Water | DI water | 77 wt % |
| Fragrance formulation | Fragrance #5 | 3 wt % |
| First Organic Solvent | Ethanol | 13 wt % |

SCJ3 Mod hex1

| | | |
|---|---|---|
| Second Organic Solvent | 1,2-hexanediol | 7 wt % |
| Properties | VOC Content (wt %) (without fragrance) | 13 wt % |
| | Solubility, RT | Clear |
| | Solubility, 5° C. | Hazy |

Example 51

SCJ3 Mod hex2

| | | |
|---|---|---|
| Water | DI water | 79 wt % |
| Fragrance formulation | Fragrance #5 | 3 wt % |
| First Organic Solvent | Ethanol | 13 wt % |
| Second Organic Solvent | 1,2-hexanediol | 5 wt % |
| Properties | VOC Content (wt %) (without fragrance) | 13 wt % |
| | Solubility, RT | Clear |
| | Solubility, 5° C. | Hazy |

Example 52

SCJ3 Mod PM1

| | | |
|---|---|---|
| Water | DI water | 71 wt % |
| Fragrance formulation | Fragrance #5 | 3 wt % |
| First Organic Solvent | Ethanol | 11 wt % |
| Second Organic Solvent | Propylene Glycol Methyl Ether | 6 wt % |
| | 1,2-hexanediol | 9 wt % |
| Properties | VOC Content (wt %) (without fragrance) | 17 wt % |
| | Solubility, RT | Clear |
| | Solubility, 5° C. | Clear |

Example 53

SCJ1 - Fragrance #6

| | | |
|---|---|---|
| Water | Deionized (DI) water | 70 wt % |
| Fragrance formulation | Fragrance #6 | 3 wt % |
| First Organic Solvent | Ethanol | 17 wt % |
| Second Organic Solvent | Dipropylene glycol | 10 wt % |
| Properties | VOC Content (wt %) (without fragrance) | 17 wt % |
| | Solubility, RT | Clear |
| | Solubility, 5° C. | Clear |

Example 54

SCJ1 Mod DPM1

| | | |
|---|---|---|
| Water | DI water | 70 wt % |
| Fragrance formulation | Fragrance #6 | 3 wt % |
| First Organic Solvent | Ethanol | 11 wt % |
| Second Organic Solvent | DiPropylene Glycol Methyl Ether | 6 wt % |
| | Dipropylene glycol | 10 wt % |

-continued

| SCJ1 Mod DPM1 | | |
|---|---|---|
| Properties | VOC Content (wt %) (without fragrance) | 17 wt % |
| | Solubility, RT | Clear |
| | Solubility, 5° C. | Clear |

Example 55

| SCJ1 Mod PM1 | | |
|---|---|---|
| Water | DI water | 70 wt % |
| Fragrance formulation | Fragrance #6 | 3 wt % |
| First Organic Solvent | Ethanol | 11 wt % |
| Second Organic Solvent | Propylene Glycol Methyl Ether | 6 wt % |
| | Dipropylene glycol | 10 wt % |
| Properties | VOC Content (wt %) (without fragrance) | 17 wt % |
| | Solubility, RT | Clear |
| | Solubility, 5° C. | Clear |

Example 56

| SCJ3 Mod PMA1 | | |
|---|---|---|
| Water | DI water | 71 wt % |
| Fragrance formulation | Fragrance #6 | 3 wt % |
| First Organic Solvent | Ethanol | 11 wt % |
| Second Organic Solvent | Propylene Glycol Methyl Ether Acetate | 6 wt % |
| | 1,2-hexanediol | 9 wt % |
| Properties | VOC Content (wt %) (without fragrance) | 17 wt % |
| | Solubility, RT | Clear |
| | Solubility, 5° C. | Clear |

Example 57

| SCJ3 Mod DPM1 | | |
|---|---|---|
| Water | DI water | 71 wt % |
| Fragrance formulation | Fragrance #6 | 3 wt % |
| First Organic Solvent | Ethanol | 11 wt % |
| Second Organic Solvent | DiPropylene Glycol Methyl Ether | 6 wt % |
| | 1,2-hexanediol | 9 wt % |
| Properties | VOC Content (wt %) (without fragrance) | 17 wt % |
| | Solubility, RT | Clear |
| | Solubility, 5° C. | Clear |

Example 58

| SCJ3 Mod hex1 | | |
|---|---|---|
| Water | DI water | 77 wt % |
| Fragrance formulation | Fragrance #6 | 3 wt % |
| First Organic Solvent | Ethanol | 13 wt % |
| Second Organic Solvent | 1,2-hexanediol | 7 wt % |

-continued

| SCJ3 Mod hex1 | | |
|---|---|---|
| Properties | VOC Content (wt %) (without fragrance) | 13 wt % |
| | Solubility, RT | Clear |
| | Solubility, 5° C. | Clear |

Example 59

| SCJ3 Mod hex2 | | |
|---|---|---|
| Water | DI water | 79 wt % |
| Fragrance formulation | Fragrance #6 | 3 wt % |
| First Organic Solvent | Ethanol | 13 wt % |
| Second Organic Solvent | 1,2-hexanediol | 5 wt % |
| Properties | VOC Content (wt %) (without fragrance) | 13 wt % |
| | Solubility, RT | Clear |
| | Solubility, 5° C. | Clear |

Example 60

| SCJ3 Mod PM1 | | |
|---|---|---|
| Water | DI water | 71 wt % |
| Fragrance formulation | Fragrance #6 | 3 wt % |
| First Organic Solvent | Ethanol | 11 wt % |
| Second Organic Solvent | Propylene Glycol Methyl Ether | 6 wt % |
| | 1,2-hexanediol | 9 wt % |
| Properties | VOC Content (wt %) (without fragrance) | 17 wt % |
| | Solubility, RT | Clear |
| | Solubility, 5° C. | Clear |

Example 61

| Sample 5-017 | | |
|---|---|---|
| Water | DI water | 79 wt % |
| Fragrance formulation | Fragrance #1 | 3 wt % |
| First Organic Solvent | Acetone | 5 wt % |
| Second Organic Solvent | Dimethoxymethane | 8 wt % |
| | Propylene glycol | 5 wt % |
| Properties | VOC Content (wt %) (without fragrance) | 8 wt % |
| | Solubility, RT | Clear |
| | Solubility, 5° C. | Clear |
| | Solubility, −18° C. | Clear |

Example 62

| Sample 5-032 | | |
|---|---|---|
| Water | DI water | 75.5 wt % |
| Fragrance formulation | Fragrance #1 | 1.5 wt % |
| First Organic Solvent | Acetone | 5 wt % |
| Second Organic Solvent | Propylene glycol monoethyl ether | 8 wt % |
| | 1,2-hexanediol | 10 wt % |

-continued

Sample 5-032

| | | |
|---|---|---|
| Properties | VOC Content (wt %) (without fragrance) | 8 wt % |
| | Solubility, RT | Clear |
| | Solubility, 5° C. | Clear |
| | Solubility, −18° C. | Clear |

Example 63

Sample 5-063

| | | |
|---|---|---|
| Water | DI water | 71.5 wt % |
| Fragrance formulation | Fragrance #1 | 1.5 wt % |
| First Organic Solvent | Acetone | 5 wt % |
| Second Organic Solvent | Acetonitrile | 12 wt % |
| | Propylene Glycol n-Propyl Ether | 10 wt % |
| Properties | VOC Content (wt %) (without fragrance) | 12 wt % |
| | Solubility, RT | Clear |
| | Solubility, 5° C. | Clear |
| | Solubility, −18° C. | Clear |

Example 64

Sample 5-64

| | | |
|---|---|---|
| Water | DI water | 75 wt % |
| Fragrance formulation | Fragrance #1 | 3 wt % |
| First Organic Solvent | Isopropanol | 5 wt % |
| Second Organic Solvent | Propylene Glycol Methyl Ether Acetate | 12 wt % |
| | 1,2-hexanediol | 5 wt % |
| Properties | VOC Content (wt %) (without fragrance) | 17 wt % |
| | Solubility, RT | Clear |
| | Solubility, 5° C. | Clear |
| | Solubility, −18° C. | Clear |

Example 65

Sample 5-144

| | | |
|---|---|---|
| Water | DI water | 76.5 wt % |
| Fragrance formulation | Fragrance #1 | 1.5 wt % |
| First Organic Solvent | Isopropanol | 5 wt % |
| Second Organic Solvent | Propylene glycol monoethyl ether | 12 wt % |
| | Propylene Glycol n-Propyl Ether | 5 wt % |
| Properties | VOC Content (wt %) (without fragrance) | 17 wt % |
| | Solubility, RT | Clear |
| | Solubility, 5° C. | Clear |
| | Solubility, −18° C. | Clear |

Example 66

Sample 6-028

| | | |
|---|---|---|
| Water | DI water | 77 wt % |
| Fragrance formulation | Fragrance #1 | 3 wt % |
| First Organic Solvent | Ethanol | 5 wt % |
| Second Organic Solvent | Propylene glycol monoethyl ether | 5 wt % |
| | 1,2-hexanediol | 10 wt % |
| Properties | VOC Content (wt %) (without fragrance) | 10 wt % |
| | Solubility, RT | Clear |
| | Solubility, 5° C. | Clear |
| | Solubility, −18° C. | Clear |

Example 67

Sample 6-134

| | | |
|---|---|---|
| Water | DI water | 79.5 wt % |
| Fragrance formulation | Fragrance #1 | 1.5 wt % |
| First Organic Solvent | Ethanol | 9 wt % |
| Second Organic Solvent | Ethylene Glycol Mono n-Propyl Ether | 5 wt % |
| | Propylene Glycol n-Propyl Ether | 5 wt % |
| Properties | VOC Content (wt %) (without fragrance) | 14 wt % |
| | Solubility, RT | Clear |
| | Solubility, 5° C. | Clear |
| | Solubility, −18° C. | Clear |

Example 68

Sample SCJ1 Mod PG1

| | | |
|---|---|---|
| Water | DI water | 70 wt % |
| Fragrance formulation | Fragrance #1 | 3 wt % |
| First Organic Solvent | Ethanol | 11 wt % |
| Second Organic Solvent | Propylene Glycol | 6 wt % |
| | Dipropylene Glycol | 10 wt % |
| Properties | VOC Content (wt %) (without fragrance) | 11 wt % |
| | Solubility, RT | Clear |
| | Solubility, 5° C. | Clear |
| | Flashpoint (° F.) | 104° F. |
| | Refractive Index @ 20° C. | 1.36 |

Example 69

Sample SCJ1 Mod PG1

| | | |
|---|---|---|
| Water | DI water | 70 wt % |
| Fragrance formulation | Fragrance #3 | 3 wt % |
| First Organic Solvent | Ethanol | 11 wt % |
| Second Organic Solvent | Propylene Glycol | 6 wt % |
| | Dipropylene Glycol | 10 wt % |
| Properties | VOC Content (wt %) (without fragrance) | 11 wt % |
| | Solubility, RT | Clear |
| | Solubility, 5° C. | Clear |
| | Flashpoint (° F.) | 104° F. |
| | Refractive Index @ 20° C. | 1.36 |

Example 70

| | Sample SCJ1 Mod PG1 | |
|---|---|---|
| Water | DI water | 70 wt % |
| Fragrance formulation | Fragrance #4 | 3 wt % |
| First Organic Solvent | Ethanol | 11 wt % |
| Second Organic Solvent | Propylene Glycol | 6 wt % |
| | Dipropylene Glycol | 10 wt % |
| Properties | VOC Content (wt %) (without fragrance) | 11 wt % |
| | Solubility, RT | Clear |
| | Solubility, 5° C. | Clear |
| | Flashpoint (° F.) | 107.6° F. |
| | Refractive Index @ 20° C. | 1.36 |

Example 71

| | Sample SCJ1 Mod PG1 | |
|---|---|---|
| Water | DI water | 70 wt % |
| Fragrance formulation | Fragrance #6 | 3 wt % |
| First Organic Solvent | Ethanol | 11 wt % |
| Second Organic Solvent | Propylene Glycol | 6 wt % |
| | Dipropylene Glycol | 10 wt % |
| Properties | VOC Content (wt %) (without fragrance) | 11 wt % |
| | Solubility, RT | Clear |
| | Solubility, 5° C. | Clear |
| | Flashpoint (° F.) | 104° F. |
| | Refractive Index @ 20° C. | 1.36 |

Example 72

| | Sample SCJ1 Mod DPG1 | |
|---|---|---|
| Water | DI water | 76 wt % |
| Fragrance formulation | Fragrance #1 | 3 wt % |
| First Organic Solvent | Ethanol | 11 wt % |
| Second Organic Solvent | Dipropylene Glycol | 10 wt % |
| Properties | VOC Content (wt %) (without fragrance) | 11 wt % |
| | Solubility, RT | Clear |
| | Solubility, 5° C. | Clear |
| | Flashpoint (° F.) | 122° F. |
| | Refractive Index @ 20° C. | 1.36 |

Example 73

| | Sample SCJ1 Mod DPG2 | |
|---|---|---|
| Water | DI water | 71 wt % |
| Fragrance formulation | Fragrance #1 | 3 wt % |
| First Organic Solvent | Ethanol | 11 wt % |
| Second Organic Solvent | Dipropylene Glycol | 15 wt % |
| Properties | VOC Content (wt %) (without fragrance) | 11 wt % |
| | Solubility, RT | Clear |
| | Solubility, 5° C. | Clear |
| | Flashpoint (° F.) | 104° F. |
| | Refractive Index @ 20° C. | 1.36 |

Example 74

| | Sample SCJ1 Mod EtOH-2 | |
|---|---|---|
| Water | DI water | 74 wt % |
| Fragrance formulation | Fragrance #1 | 3 wt % |
| First Organic Solvent | Ethanol | 13 wt % |
| Second Organic Solvent | Dipropylene Glycol | 10 wt % |
| Properties | VOC Content (wt %) (without fragrance) | 13 wt % |
| | Solubility, RT | Clear |
| | Solubility, 5° C. | Clear |
| | Flashpoint (° F.) | 98.6° F. |
| | Refractive Index @ 20° C. | 1.36 |

Example 75

| | Sample SCJ1 Mod EtOH-3 | |
|---|---|---|
| Water | DI water | 72 wt % |
| Fragrance formulation | Fragrance #1 | 3 wt % |
| First Organic Solvent | Ethanol | 15 wt % |
| Second Organic Solvent | Dipropylene Glycol | 10 wt % |
| Properties | VOC Content (wt %) (without fragrance) | 15 wt % |
| | Solubility, RT | Clear |
| | Solubility, 5° C. | Clear |
| | Flashpoint (° F.) | 97° F. |
| | Refractive Index @ 20° C. | 1.36 |

Example 76

| | Sample SCJ1 Mod DPG1 | |
|---|---|---|
| Water | DI water | 76 wt % |
| Fragrance formulation | Fragrance #3 | 3 wt % |
| First Organic Solvent | Ethanol | 11 wt % |
| Second Organic Solvent | Dipropylene Glycol | 10 wt % |
| Properties | VOC Content (wt %) (without fragrance) | 11 wt % |
| | Solubility, RT | Clear |
| | Solubility, 5° C. | Clear |
| | Flashpoint (° F.) | 122° F. |
| | Refractive Index @ 20° C. | 1.36 |

Example 77

| | Sample SCJ1 Mod DPG1 | |
|---|---|---|
| Water | DI water | 76 wt % |
| Fragrance formulation | Fragrance #4 | 3 wt % |
| First Organic Solvent | Ethanol | 11 wt % |
| Second Organic Solvent | Dipropylene Glycol | 10 wt % |
| Properties | VOC Content (wt %) (without fragrance) | 11 wt % |
| | Solubility, RT | Clear |
| | Solubility, 5° C. | Clear |
| | Flashpoint (° F.) | 122° F. |
| | Refractive Index @ 20° C. | 1.36 |

Example 78

| | Sample SCJ1 Mod DPG1 | |
|---|---|---|
| Water | DI water | 76 wt % |
| Fragrance formulation | Fragrance #6 | 3 wt % |
| First Organic Solvent | Ethanol | 11 wt % |
| Second Organic Solvent | Dipropylene Glycol | 10 wt % |
| Properties | VOC Content (wt %) (without fragrance) | 11 wt % |
| | Solubility, RT | Clear |
| | Solubility, 5° C. | Clear |
| | Flashpoint (° F.) | 122° F. |
| | Refractive Index @ 20° C. | 1.36 |

Example 79

| | Sample SCJ1 Mod EtOH-2 | |
|---|---|---|
| Water | DI water | 74 wt % |
| Fragrance formulation | Fragrance #3 | 3 wt % |
| First Organic Solvent | Ethanol | 13 wt % |
| Second Organic Solvent | Dipropylene Glycol | 10 wt % |
| Properties | VOC Content (wt %) (without fragrance) | 13 wt % |
| | Solubility, RT | Clear |
| | Solubility, 5° C. | Clear |
| | Flashpoint (° F.) | 98.6° F. |
| | Refractive Index @ 20° C. | 1.36 |

Example 80

| | Sample SCJ1 Mod EtOH-2 | |
|---|---|---|
| Water | DI water | 74 wt % |
| Fragrance formulation | Fragrance #4 | 3 wt % |
| First Organic Solvent | Ethanol | 13 wt % |
| Second Organic Solvent | Dipropylene Glycol | 10 wt % |
| Properties | VOC Content (wt %) (without fragrance) | 13 wt % |
| | Solubility, RT | Clear |
| | Solubility, 5° C. | Clear |
| | Flashpoint (° F.) | 102° F. |
| | Refractive Index @ 20° C. | 1.36 |

Example 81

| | Sample SCJ1 Mod EtOH-2 | |
|---|---|---|
| Water | DI water | 74 wt % |
| Fragrance formulation | Fragrance #6 | 3 wt % |
| First Organic Solvent | Ethanol | 13 wt % |
| Second Organic Solvent | Dipropylene Glycol | 10 wt % |
| Properties | VOC Content (wt %) (without fragrance) | 13 wt % |
| | Solubility, RT | Clear |
| | Solubility, 5° C. | Clear |
| | Flashpoint (° F.) | 100° F. |
| | Refractive Index @ 20° C. | 1.36 |

Any of the embodiments described herein may be modified to include any of the structures or methodologies disclosed in connection with other embodiments.

All documents cited in the Detailed Description are, in relevant part, incorporated herein by reference; the citation of any document is not to be construed as an admission that it is prior art with respect to the present invention.

INDUSTRIAL APPLICABILITY

The present disclosure provides water-based fragrance compositions, devices for emission of water-based fragrance compositions, and methods for emitting long-lasting scent. The water-based fragrance compositions generally include an increased amount of water, which allows for continuous emission, if desired. The water-based fragrance compositions may also be free of materials with a boiling point greater than about 300 degrees C.

Numerous modifications to the present disclosure will be apparent to those skilled in the art in view of the foregoing description. Accordingly, this description is to be construed as illustrative only and is presented for the purpose of enabling those skilled in the art to make and use the embodiments of the present disclosure and to teach the best mode of carrying out same. The exclusive rights to all modifications which come within the scope of the appended claims are reserved.

We claim:

1. A water-based fragrance composition consisting of:
   a) at least about 67 wt % water;
   b) between 11 wt % and 17 wt % ethanol;
   c) between about 0.05 wt % and about 5 wt % of a fragrance formulation comprising one or more perfume raw materials having a Log $P_{octonol-water}$ (Log $P_{OW}$) less than 2.0 and a Log $P_{hexane-water}$ (Log $P_{HW}$) less than 1.0; and
   d) between 10 wt % and 22 wt % of an organic solvent selected from the group consisting of dipropylene glycol methyl ether; propylene glycol methyl ether; dipropylene glycol; propylene glycol; pentylene glycol; caprylyl glycol; 1,2-hexanediol; propylene glycol methyl ether acetate; dipropylene glycol methyl ether acetate; propylene glycol monopropyl ether; ethylene glycol mono n-propyl ether; propylene glycol monoethyl ether; diethylene glycol monobutyl ether; ethylene glycol monohexyl ether; dimethoxymethane; dimethylsulfoxide, acetonitrile; and combinations thereof, wherein total volatile organic compound content in the water-based fragrance composition is between 14 wt % and 18 wt %, and wherein the total of the ethanol and the organic solvent of d) is at least 26 wt %.

2. The water-based fragrance composition of claim 1, wherein the fragrance formulation is free of any material with a boiling point greater than about 300° C.

3. The water-based fragrance composition of claim 1, wherein the organic solvent of d) may be free of volatile organic compounds.

4. The water-based fragrance composition of claim 1, wherein the water, the fragrance formulation, the ethanol, and the organic solvent of d) form a homogenous liquid phase.

5. The water-based fragrance composition of claim 1, wherein the water-based fragrance composition comprises between about 0.05 and about 3 wt % of the fragrance formulation.

6. The water-based fragrance composition of claim 1, wherein the organic solvent of d) consists of dipropylene glycol methyl ether and dipropylene glycol.

7. The water-based fragrance composition of claim 1, wherein the water-based fragrance composition consists of 70 wt % water, 11 wt % ethanol, 3 wt % of the fragrance formulation, 6 wt % dipropylene glycol methyl ether, and 10 wt % dipropylene glycol.

8. The water-based fragrance composition of claim 1, wherein the organic solvent of d) consists of dipropylene glycol methyl ether and 1,2-hexanediol.

9. A method of providing a long-lasting scent consisting of delivering boluses of droplets into air, wherein a vibrating mesh nebulizer converts only a single liquid water-based fragrance composition into the droplets, and wherein the liquid water-based fragrance composition consists of: a) at least about 67 wt % water; b) between 11 wt % and 17 wt % ethanol; c) between about 0.05 wt % and about 5 wt % of a fragrance formulation comprising one or more perfume raw materials having a Log $P_{octonol\text{-}water}$ (Log $P_{OW}$) less than 2.0 and a Log $P_{hexane\text{-}water}$ (Log $P_{HW}$) less than 1.0; and d) between 10 wt % and 22 wt % of an organic solvent selected from the group consisting of dipropylene glycol methyl ether; propylene glycol methyl ether; dipropylene glycol; propylene glycol; pentylene glycol; caprylyl glycol; 1,2-hexanediol; propylene glycol methyl ether acetate; dipropylene glycol methyl ether acetate; propylene glycol monopropyl ether; ethylene glycol mono n-propyl ether; propylene glycol monoethyl ether; diethylene glycol monobutyl ether; ethylene glycol monohexyl ether; dimethoxymethane; dimethylsulfoxide, acetonitrile; and combinations thereof, and wherein total volatile organic compound content in the water-based fragrance composition is between 14 wt % and 18 wt %, and wherein the total of the ethanol and the organic solvent is at least 26 wt %.

10. The method of claim 9, wherein the water-based fragrance composition has a pH between about 3 and about 10.

* * * * *